United States Patent
Haase

[11] Patent Number: 5,993,383
[45] Date of Patent: Nov. 30, 1999

[54] LARYNGOSCOPE BLADE WITH TONGUE CONTROLLING WING SECTIONS

[76] Inventor: Brian J. Haase, 2080 NE. 56th St., #1, Fort Lauderdale, Fla. 33308

[21] Appl. No.: 09/321,260

[22] Filed: May 27, 1999

[51] Int. Cl.⁶ .................................................. A61B 1/267
[52] U.S. Cl. .......................................... 600/191; 600/190
[58] Field of Search ................................ 600/190, 191, 600/199, 192, 240, 241, 185, 193, 194, 195, 196

[56] References Cited

U.S. PATENT DOCUMENTS

| | | | |
|---|---|---|---|
| 3,397,687 | 8/1968 | Kirchdoerfer | 600/240 |
| 3,856,001 | 12/1974 | Phillips | 600/199 |
| 3,943,920 | 3/1976 | Kandel | 128/11 |
| 4,295,465 | 10/1981 | Racz | 128/11 |
| 4,314,551 | 2/1982 | Kadell | 600/190 |
| 4,573,451 | 3/1986 | Bauman | 128/11 |
| 5,003,962 | 4/1991 | Choi | 128/11 |
| 5,575,758 | 11/1996 | Easterbrook, III | 600/193 |
| 5,603,688 | 2/1997 | Upsher | 600/190 |
| 5,702,351 | 12/1997 | Bar-Or et al. | 600/190 |

*Primary Examiner*—Paul J. Hirsch
*Attorney, Agent, or Firm*—Joseph N. Breaux

[57] ABSTRACT

An improved laryngoscope blade of the type having a laryngoscope handle attachment fitting and a blade assembly including an illumination source having a light output and a straight blade member with curved end extending from the handle attachment fitting and defining a visualization channel into which the light output of the illumination source is directed. The improvement includes providing left and right frustrum shaped, mirror image wing sections on the straight blade member with curved end for controlling and depressing the tongue out of the line of sight when inserting a tube.

1 Claim, 1 Drawing Sheet

5,993,383

LARYNGOSCOPE BLADE WITH TONGUE CONTROLLING WING SECTIONS

TECHNICAL FIELD

The present invention relates to laryngoscope blades and more particularly to an improved laryngoscope blade of the type having a laryngoscope handle attachment fitting and a blade assembly including an illumination source having a light output and a straight blade member with curved end extending from the handle attachment fitting and defining a visualization channel into which the light output of the illumination source is directed and wherein the improvement comprises left and right frustrum shaped, mirror image wing sections for controlling and depressing the tongue out of the line of sight when inserting a tube; each of the left and right frustrum shaped, mirror image wing sections extending outwardly from an opposed side edge of the blade member a distance of between one-quarter and one and one-half inches and having a leading wing section edge positioned a distance of less than three inches from the curved tip end, the leading wing section edge being oriented at an angle of between one-hundred fifteen and one-hundred fifty degrees with respect to the side edge from which it extends.

BACKGROUND ART

Emergency medical treatment often requires a tube to be inserted past the tongue and through the vocal cords to facilitate breathing or the like. The tube is typically inserted with the assistance of a laryngoscope having a laryngoscope blade that is used to guide the tube past the tongue and through the vocal cords. Because the tongue can prevent medical personal from seeing the vocal cords, it would be a benefit to have a laryngoscope blade that included a pair of wing sections for controlling and depressing the tongue out of the line of sight when inserting a tube.

GENERAL SUMMARY DISCUSSION OF INVENTION

It is thus an object of the invention to provide an improved laryngoscope blade with tongue controlling wing sections.

It is a further object of the invention to provide an improved laryngoscope blade wherein the improvement comprises left and right frustrum shaped, mirror image wing sections for controlling and depressing the tongue out of the line of sight when inserting a tube; each of the left and right frustrum shaped, mirror image wing sections extending outwardly from an opposed side edge of the blade member a distance of between one-quarter and one and one-half inches and having a leading wing section edge positioned a distance of less than three inches from the curved tip end, the leading wing section edge being oriented at an angle of between one-hundred fifteen and one-hundred fifty degrees with respect to the side edge from which it extends.

It is a still further object of the invention to provide a laryngoscope blade with tongue controlling wing sections that accomplishes all or some of the above objects in combination.

Accordingly, an improved laryngoscope blade of the type having a laryngoscope handle attachment fitting and a blade assembly including an illumination source having a light output and a straight blade member with curved end extending from the handle attachment fitting and defining a visualization channel into which the light output of the illumination source is directed and wherein the improvement comprises left and right frustrum shaped, mirror image wing sections for controlling and depressing the tongue out of the line of sight when inserting a tube; each of the left and right frustrum shaped, mirror image wing sections extending outwardly from an opposed side edge of the blade member a distance of between one-quarter and one and one-half inches and having a leading wing section edge positioned a distance of less than three inches from the curved tip end, the leading wing section edge being oriented at an angle of between one-hundred fifteen and one-hundred fifty degrees with respect to the side edge from which it extends. The wing sections are preferably of length between one and four inches.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein.

EXEMPLARY MODE FOR CARRYING OUT THE INVENTION

Figure 1:
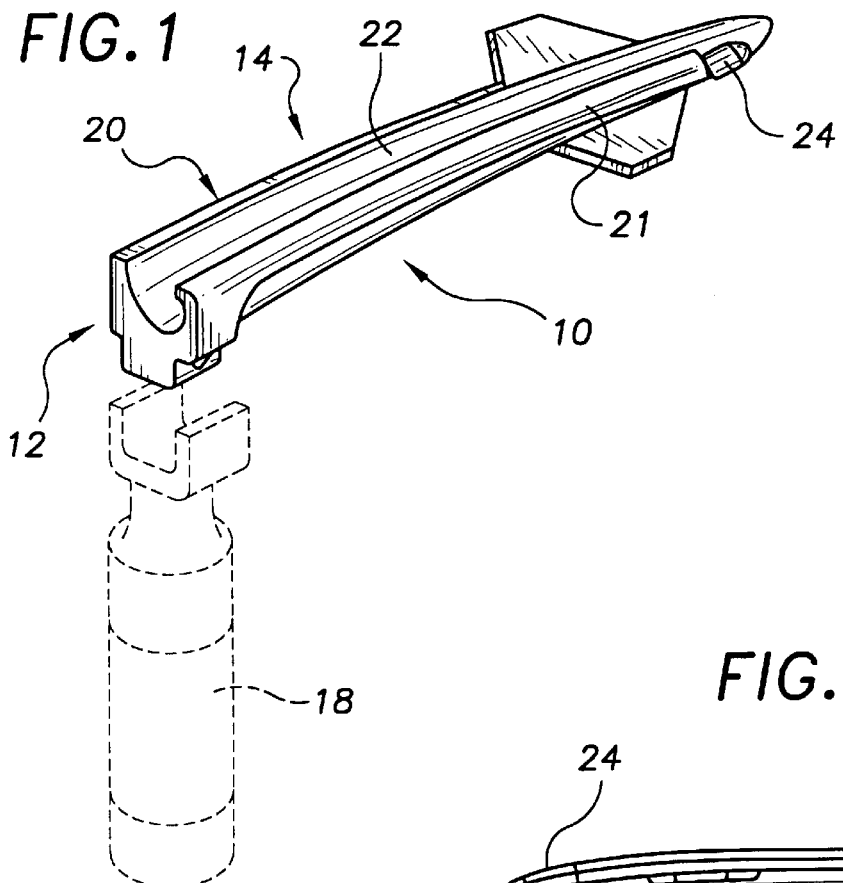
FIG. 1 is a perspective view of an exemplary embodiment of the laryngoscope blade of the present invention showing the laryngoscope handle attachment fitting and a blade assembly including an illumination source having a light output and a straight blade member with curved end extending from the handle attachment fitting and defining a visualization channel into which the light output of the illumination source is directed and wherein the improvement comprises left and right frustrum shaped, mirror image wing sections for controlling and depressing the tongue out of the line of sight when inserting a tube; each of the left and right frustrum shaped, mirror image wing sections extending outwardly from an opposed side edge of the blade member a distance of between one-quarter and one and one-half inches and having a leading wing section edge positioned a distance of less than three inches from the curved tip end, the leading wing section edge being oriented at an angle of between one-hundred fifteen and one-hundred fifty degrees with respect to the side edge from which it extends.

FIG. 1 shows an exemplary embodiment of the improved laryngoscope blade of the present invention generally designated 10. Laryngoscope blade 10 includes a laryngoscope handle attachment fitting, generally designated 12, and a blade assembly, generally designated 14. Handle attachment fitting 12 is used to attach laryngoscope blade 10 to a conventional attachment handle 18, (shown in dashed lines).

Figure 2:
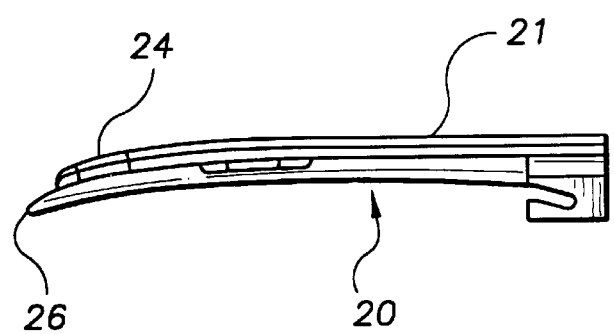
FIG. 2 is a side plan view showing the exemplary laryngoscope blade of FIG. 1 including the laryngoscope handle attachment fitting and the straight blade member with curved end of the blade assembly.

Blade assembly 14 includes a curved, seven and one-half inch long stainless steel blade member, generally designated 20, that extends from handle attachment fitting 12 and defines a visualization channel 22 into which the output from a one inch long illumination source 24 is directed to aid the user in visualizing the vocal cords. A partial five and one-half inch long cover 21 is provided over a section of visualization channel to further assist visualization of the vocal cords. Visualization channel 22 terminates, with reference now to FIG. 2, at a location just past the start of illumination source 24.

Figure 3:
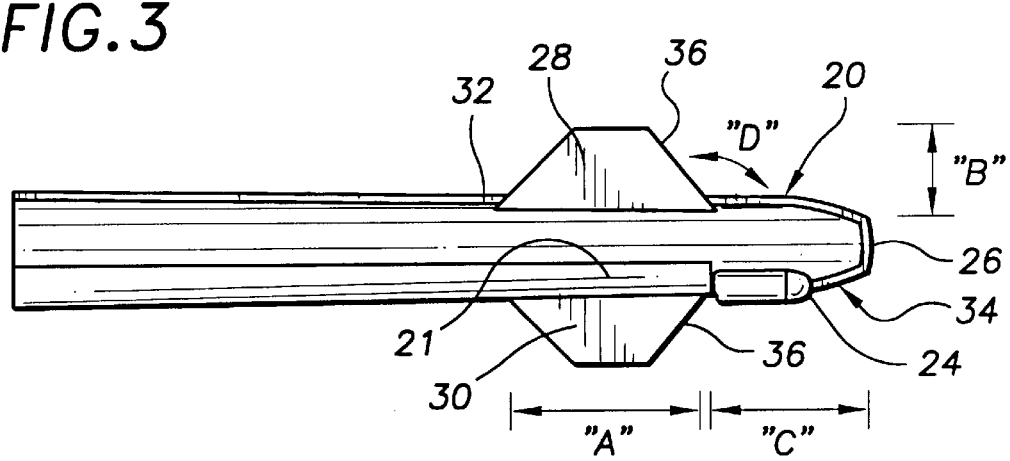
FIG. 3 is a top plan view of the straight blade member with curved end of the blade assembly showing the visualization channel, the illumination source light output is directed into the visualization channel, and the left and right frustrum shaped, mirror image wing sections each being of a length "A" of two inches, extending outwardly from its respective side edge a distance "B" of one-half inch and having a leading wing section edge positioned a distance "C" of two inches from the curved tip end, the leading wing section edge being oriented at an angle "D" of one-hundred forty degrees with respect to the side edge from which it extends.

Referring now to FIG. 3, straight blade member with curved end 20 includes left and right frustrum shaped, mirror image wing sections 28,30 each being of a length "A" of two inches; extending outwardly from opposed side edges 32,34 thereof a distance "B" of one-half inch and having a leading wing section edge 36 positioned a distance "C" of two inches from curved tip end 26. Each leading wing section edge 36 is oriented at an angle "D" of one-hundred forty degrees with respect to the side edge 32,34 from which it extends. Dimensions "A", "B", and "C" are selected to be proportional to the length of blade member 20 which is select to correspond to the size of the patient from neonate to adult.

It can be seen from the preceding description that an improved laryngoscope blade has been provided wherein the improvement comprises left and right frustrum shaped, mirror image wing sections for controlling and depressing the tongue out of the line of sight when inserting a tube; each of the left and right frustrum shaped, mirror image wing sections extending outwardly from an opposed side edge of the blade member a distance of between one-quarter and one and one-half inches and having a leading wing section edge positioned a distance of less than three inches from the curved tip end, the leading wing section edge being oriented at an angle of between one-hundred fifteen and one-hundred fifty degrees with respect to the side edge from which it extends.

It is noted that the embodiment of the laryngoscope blade with tongue controlling wing sections described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. An improved laryngoscope blade having a laryngoscope handle attachment fitting and a blade assembly including an illumination source having a light output and a straight blade member with a curved end extending from the handle attachment fitting and defining a visualization channel into which the output of the illumination source is directed, the improvement comprising:

left and right frustrum shaped, mirror image wing sections;

each of said left and right frustrum shaped, mirror image wing sections extending outwardly from an opposed side edge of the blade member a distance of between one-quarter and one and one-half inches and having a leading wing section edge positioned a distance of less than three inches from the curved tip end, said leading wing section edge being oriented at an angle of between one-hundred fifteen and one-hundred fifty degrees with respect to the side edge from which it extends.

* * * * *